United States Patent
Hubner et al.

(10) Patent No.: US 6,790,038 B2
(45) Date of Patent: Sep. 14, 2004

(54) DENTAL VACUUM SYSTEM ASSEMBLY AND PROCESS INCORPORATING AN AMALGAM SEPARATION CHAMBER

(75) Inventors: Henry Hubner, Amityville, NY (US); Frederick R. Fischer, Farmingdale, NY (US)

(73) Assignee: Air Techniques, Inc., Hicksville, NY (US)

( * ) Notice: Subject to any disclaimer, the term of this patent is extended or adjusted under 35 U.S.C. 154(b) by 200 days.

(21) Appl. No.: 10/171,763

(22) Filed: Jun. 17, 2002

(65) Prior Publication Data

US 2003/0003417 A1 Jan. 2, 2003

Related U.S. Application Data

(60) Provisional application No. 60/300,105, filed on Jun. 25, 2001.

(51) Int. Cl.$^7$ ................................................ A61C 17/04
(52) U.S. Cl. ...................................................... 433/92
(58) Field of Search .............................. 433/91, 92, 96

(56) References Cited

U.S. PATENT DOCUMENTS

| | | | | | |
|---|---|---|---|---|---|
| 4,097,381 A | * | 6/1978 | Ritzler | ........................ | 210/259 |
| 4,564,374 A | * | 1/1986 | Hofmann | ........................ | 95/24 |
| 4,580,978 A | * | 4/1986 | Motola et al. | ................. | 433/92 |
| 4,591,437 A | * | 5/1986 | Ernryd et al. | ................ | 210/265 |
| 5,018,971 A | * | 5/1991 | Trawoger et al. | .............. | 433/92 |
| 5,330,641 A | * | 7/1994 | Cattani | ........................ | 210/188 |
| 5,667,382 A | * | 9/1997 | Holland | ........................ | 433/92 |
| 5,795,159 A | * | 8/1998 | Ralls et al. | .................... | 433/92 |
| 5,797,742 A | * | 8/1998 | Fraker | ........................ | 433/92 |
| 5,885,076 A | * | 3/1999 | Ralls et al. | .................... | 433/92 |
| 6,638,066 B2 | * | 10/2003 | Hubner et al. | ................ | 433/92 |

FOREIGN PATENT DOCUMENTS

| CA | 2 382 431 | * | 10/2003 |
|---|---|---|---|
| DE | 42 43 239 | * | 6/1994 |
| WO | WO 98/46324 | * | 10/1998 |

* cited by examiner

*Primary Examiner*—Ralph A. Lewis
(74) *Attorney, Agent, or Firm*—Louis E. Marn; Clifford G. Frayne

(57) ABSTRACT

A dental vacuum system for use in dental operatories wherein a dental aspirator tip and in the dental operatory is in fluid communication with a vacuum means for providing suction to the system, there being interposed between the aspirator tip and the vacuum means a separation chamber for the separation of effluent, and solids, including amalgam and other particulate matter from the air stream, the separation chamber being in communication with a collection chamber for the separation collection of solids, amalgam and other particulate matter, from the effluent which is discharged, the collection chamber being removably replaceable from the system for the recycling of the contents.

3 Claims, 2 Drawing Sheets

DENTAL VACUUM SYSTEM ASSEMBLY AND PROCESS INCORPORATING AN AMALGAM SEPARATION CHAMBER

RELATED APPLICATIONS

Applicant claims the benefit of provisional application No. 60/300,105, filed Jun. 25, 2001.

BACKGROUND OF THE INVENTION

1. Field of the Invention

The present invention relates to dental care facilities and in particular to a central vacuum system for dental care operatories incorporating an integrated amalgam separation system.

2. Description of the Prior Art

Modern dental facilities usually include multiple operatories and a central vacuum system. Dental aspirator tips are provided at each operatory for disposition in the patient's oral cavity to remove aerosols, liquids, solid debris and odors from the patient's mouth. Typical conventional dental vacuum systems have been far from ideal from the standpoints of noise output, vacuum intensity and flow rate characteristics, efficiency, reliability and recovery of amalgam metals, and particulate matter used or generated in the dental process.

Additionally, environmental laws at some locations now have incorporated mandatory amalgam separation in the dental suction system. The dental vacuum system of the present invention as described herein incorporates an air/liquid separation tank having an integral sedimentation amalgam separator and collector insuring capatability of the system with the current state of the law.

OBJECTS OF THE INVENTION

An object of the present invention is to provide for a novel dental vacuum system for the efficient evacuation of aerosols, liquids, solid debris and odors from the patient's mouth in a dental operatory.

A still further object of the present invention is to provide for a novel dental vacuum system having a novel air/liquid/solids separation tank which incorporates an integral amalgam separation and collection capability which is removably replaceable from the system.

SUMMARY OF THE INVENTION

A dental vacuum system for use in dental operatories in which a dental aspirator tip in the dental operatory is in fluid communication with a vacuum means for providing suction to the system, there being interposed between the dental aspirator tip and the vacuum means, a separation chamber for the separation of effluent and solids including amalgam from the air stream. Solids including amalgam and liquids are collected in the separation chamber while air is passed through for eventual venting to the atmosphere. When no vacuum is required in the operatories, a sensor turns off the vacuum means and a timer relay allows for sedimentation to occur in the chamber. Thereafter, contaminated water and solids including amalgam are drawn out to an amalgam separation and collection chamber. Contaminated water is drawn off to the drain and the process repeats itself until the amalgam collection chamber has accumulated its maximum amount of solids, including amalgam. It is then prepped for recycle and replaced with an empty amalgam collection chamber and the full chamber is sent out for recovery of precious metals and proper disposal of hazardous material.

DETAILED DESCRIPTION OF THE DRAWINGS

Figure 1:
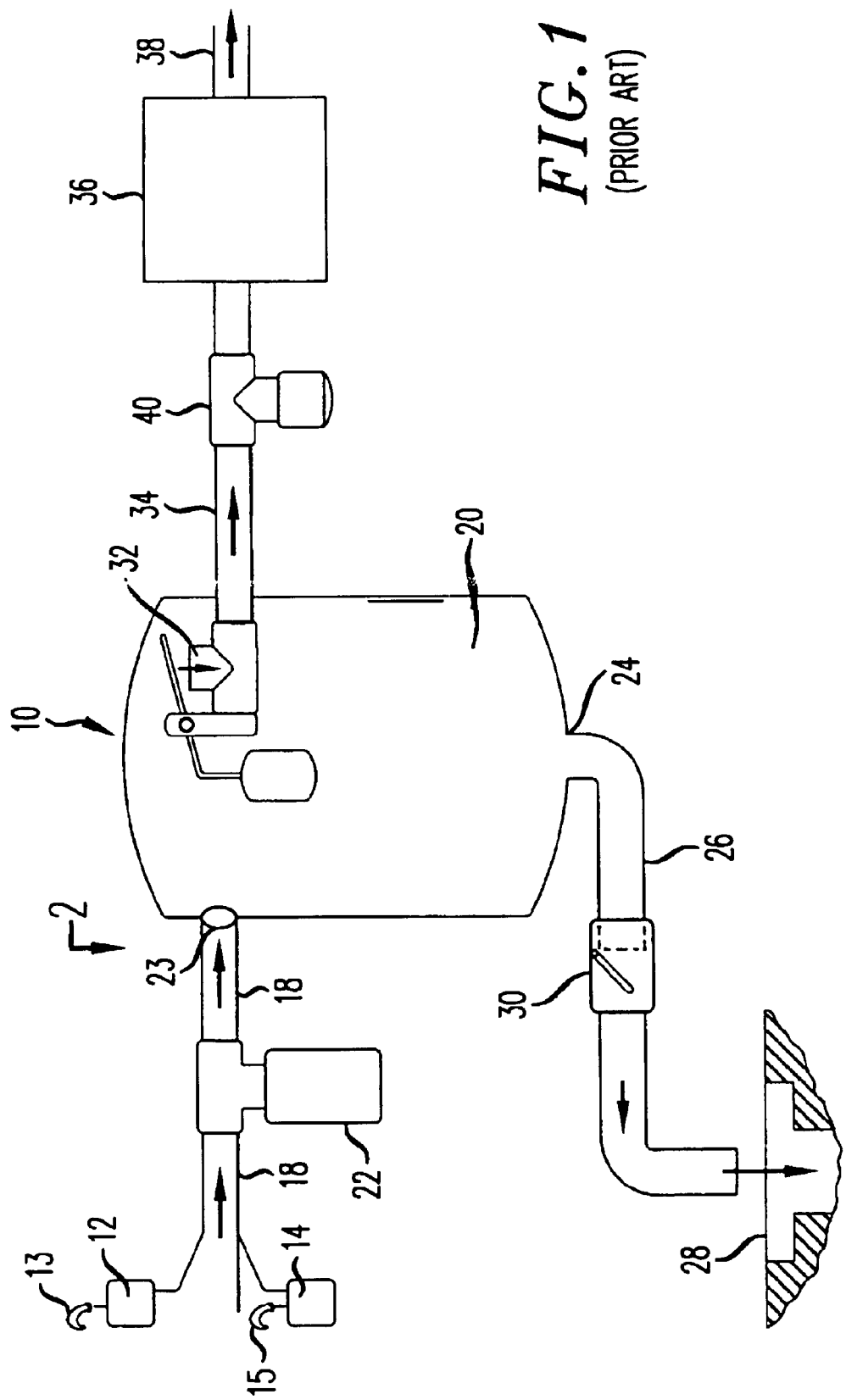
FIG. 1 is a schematic illustration of a typical dental vacuum system.

FIG. 1 is a schematic diagram of a prior art dental vacuum system 10. During the course of a dental procedure, gases, liquids and solids are removed from each dental operatory 12 and 14, by means of a dental aspirator tip 13 and 15 which are disposed within the patient's oral cavity. Gases, liquids, and solids, including amalgam under vacuum or suction are transported via conduit 18 to a separation tank 20. Disposed in conduit 18 before the separation tank 20 may be a solids collector 22 which allows gas and liquids to pass through, but interrupts the flow of large particulate solids and causes them to fall into the collector under the influence of gravity for later collection and disposal. The gas and liquids are introduced into the separator tank through inlet port 23 wherein the liquids and small particulate matter accumulate in the bottom of the tank and are subsequently drained through drain outlet 24 through conduit 26 to a sewer drain 28. A check valve 30 is positioned in conduit 26 to prevent any back flow.

The gas introduced into separation tank 20 exits separation tank 20 through a gas or air outlet port 32 to exit conduit 34 which is in communication with the vacuum pump 36 which provides the vacuum and suction to the overall system. The gas thus drawn through the system is then evacuated to the atmosphere through conduit 38. There is positioned between separator tank 20 and a vacuum pump 36 a vacuum relief valve 40.

The solids collector 22 and its location in the flow plan oftentimes presents problems in that not all solids are collected and as a result of environmental codes operatories must insure that no amalgam or metals are discharged into the sewer system.

Figure 2:
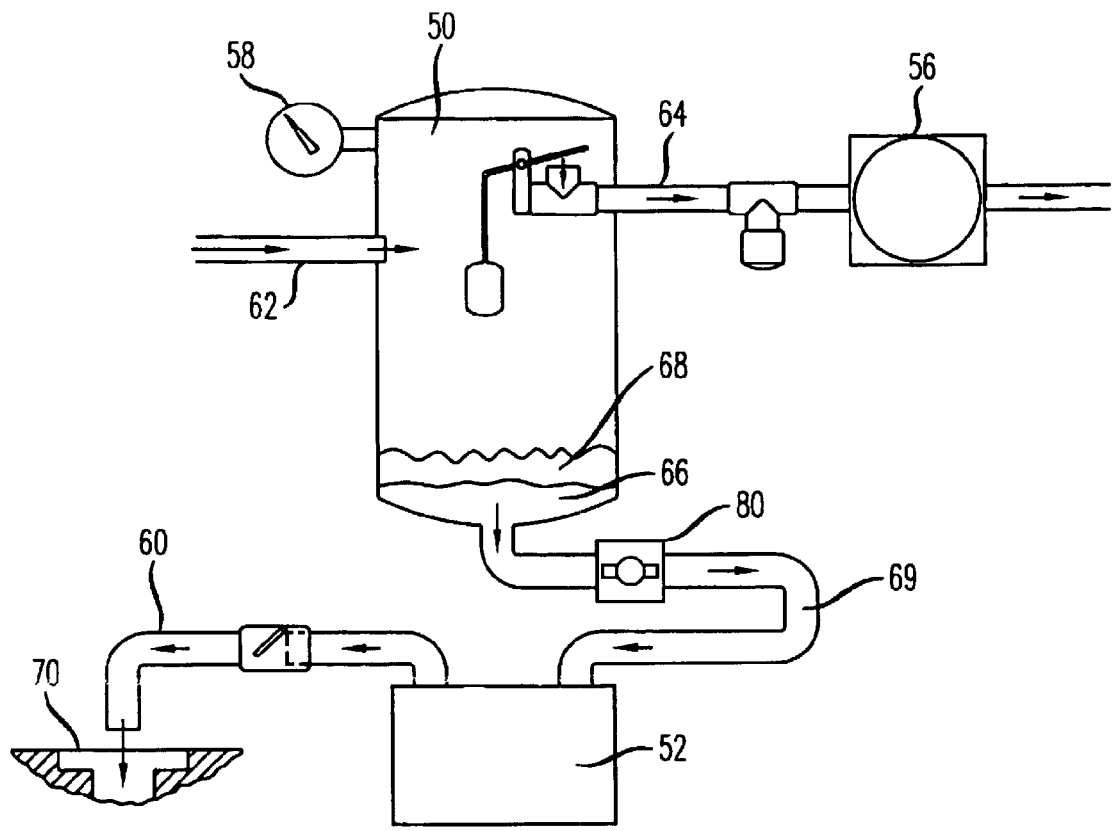
FIG. 2 is a schematic illustration of a dental vacuum system of the present invention including an amalgam separator.

FIG. 2 illustrates a dental vacuum system of the present invention with the separation chamber of the present invention further incorporating an amalgam collection chamber. The system consists of a separation/sedimentation tank 50, an amalgam collection chamber 52, the necessary control valves and a timer relay and vacuum sensor 58.

In operation, liquids, solids and gases enter the separation/sedimentation tank 50 through conduit 62 from the operatories when the vacuum system is in operation. The solids and liquids are collected and the gases are removed via conduit 64 by a vacuum pump in accordance with previous description.

When a vacuum is no longer required, the vacuum pump is turned off. The vacuum sensor 58 detects that the pump is off and starts a timer relay. The timer relay is set for a period of time which permits sedimentation 66 to occur within the separation/sedimentation tank of any solids which have been introduced therein. This results in the formation of layers or levels within tank 50, solid sedimentation 66, and a layer of contaminated water 68.

A control valve 80 is opened to permit the sedimentation/solids 66 and contaminated liquids 68 to enter a solids/amalgam collection chamber 52 via conduit 69. The control valve 80 are then closed and a vacuum may be reinitiated to the dental operatory. The preferred amalgam collection chamber 52 is of the type described in International Application PCT/SE98/00685 as published on Oct. 22, 1998, publication number WO98/46324 and the teachings thereof are incorporated herein by reference.

The solid sedimentation 66 and contaminated liquids 68 are allowed to further separate in the amalgam collection chamber 52. The contaminated water is then drawn off via conduit 60 to the sewer 70, there being positioned in conduit 60 a back flow valve 67.

The aforesaid cycle is repeated when no vacuum is required in the operatories and there is the presence of water and solids in separation tank 50 until the amalgam collection chamber 52 becomes fully charged with particulate matter or solid sedimentation 66. The amalgam collection chamber 52 is then replaced with a duplicate, and the fully charged chamber is sent to be recycled and processed for the recovery of the amalgam and other metals found therein, and proper disposal of hazardous materials.

Figure 3:
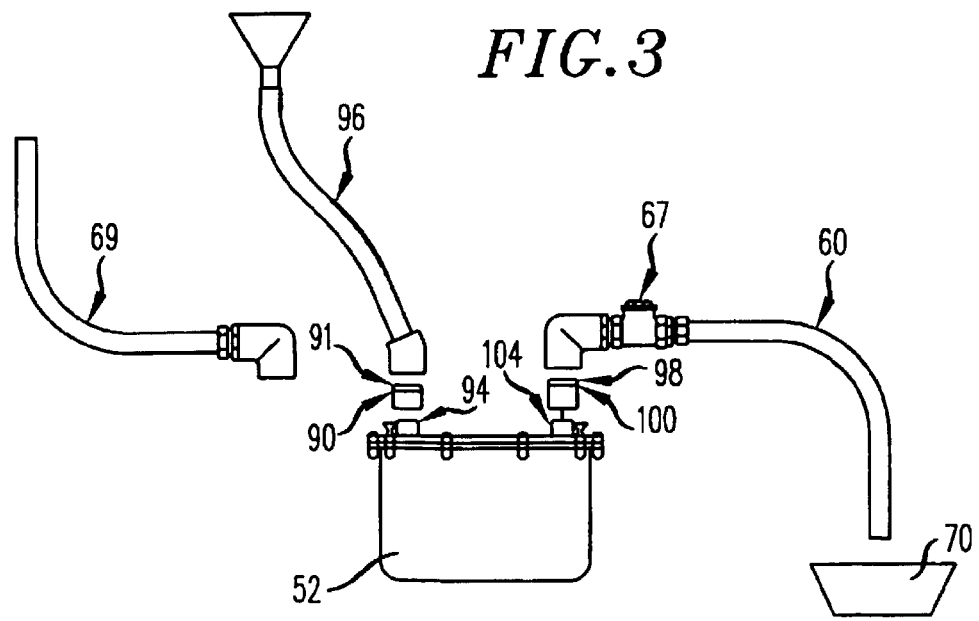
FIG. 3 is a side view illustrating the removal of a spent amalgam collection chamber.

FIG. 3 illustrates the manner of removal of an exhausted or spent amalgam collection chamber 52 so as to permit replacement and recycle the exhausted amalgam collection chamber. The process requires the power to the vacuum pump 56 be turned off and separation tank 50 be allowed to drain completely, or in the alternative the shut off valve 80 located between the separation tank 50 and the amalgam collection chamber 52 would be closed. The inlet conduit 69 to amalgam collection chamber 52 is disengaged from the adaptor 90 and O ring 92 on the inlet port 94 of the collection chamber 52. Using a funnel assembly 96 attached to the collection container inlet port 94, two liters of disinfectant solution is introduced into the amalgam collection chamber 52.

Once the two liters of disinfectant solution have been introduced, the funnel assembly 96 is removed, as is the adaptor assembly 90 and O ring 91. A shipping cap (not shown) is then placed on the inlet port 94. At this time, the outlet conduit 60, the outlet adaptor and the outlet restrictor plate 98 with O ring 100 are removed. A second shipping cap (not shown) is placed on the outlet port 104 of chamber 52. The spent collection chamber 52 is then placed in a zip lock bag and styrofoam container for shipping for recycling. The replacement container is positioned and the associated adaptors, O rings and restrictor plates are secured to the respective inlet and outlet ports. Power can then be returned to the system and respective valves returned to their proper settings.

The assembly and process disclosed insures that solids, amalgam and particulate matter from the dental operatory are collected prior to the discharge of any liquids or effluents into the sewer. Thus the possibilities of hazardous materials entering into the sewer system and water system is minimized, if not eliminated. The assembly and process insures that there is no interruption to the dental technician's work and that only air is drawn from the separation chamber and not deleterious liquids or solids which could damage the vacuum means.

While the present invention has been described with respect to the exemplary embodiment thereof, it will be recognized by those of ordinary skill in the art that many modifications and changes may be made without departing from the spirit and scope of the invention. Therefore it is manifestly intended that the invention be limited only by the claims and the equivalence thereof.

What is claimed:

1. An assembly for collection and removal of solids, amalgam and particulate matter from a dental operatory air stream created by a vacuum means comprising:

a first separation chamber positioned between a vacuum means and said dental operatory, said first separation chamber having an inlet means for the introduction of air, effluent, solids, amalgam and particulate matter from said dental operatory;

a first outlet means in communication with a vacuum source for the exhaust of air;

a second outlet means from said first separation chamber in communication with a second chamber for the exhaust of effluent, solids, amalgam and particulate matter to said second chamber for the separation of effluent from solids, amalgam and particulate matter and collection of solids, amalgam and particulate matter by gravitational sedimentation in the said second chamber, said effluent discharged to a sewer, said second chamber removably replaceable allowing for the recycling and recovery of solids, amalgam and particulate matter collected therein; and a vacuum sensor and timer relay for sensing the absence of vacuum in said first separation chamber and activating a valve for transferring said effluent, solids, amalgam and particulate matter via second outlet means to said second chamber.

2. A method for the collection and removal of effluent, solids, amalgam and particulate matter from a dental operatory air stream created by a vacuum means comprising:

a) establishing conduit communication between a vacuum means and a dental operatory;

b) positioning a first separation chamber in said conduit communication between said vacuum means and said dental operatory;

c) drawing a vacuum by means of said vacuum means from said dental operatory through said first separation chamber;

d) collecting effluent, solids, amalgam and particulate matter in said first separation chamber and permitting said residual air stream to exit to said vacuum means;

e) positioning a second separation chamber in communication with said first separation chamber;

f) exhausting said effluent, solids, amalgam and particulate matter from said first separation chamber to said second separation chamber by a valve means activated by a vacuum sensor and timer relay;

g) collecting said solids, amalgam and particulate matter in said second separation chamber by gravitational sedimentation;

h) exhausting said effluent from said second separation chamber;

i) replacing said second separation chamber when full; and j) recycling said replaced second separation chamber for recovery of said solids, amalgam and particulate matter.

3. The method in accordance with claim 2 wherein steps f through j are repeated as required by step i.

* * * * *